United States Patent
Mullaney

(10) Patent No.: US 7,938,829 B2
(45) Date of Patent: May 10, 2011

(54) ARTICULATION APPARATUS FOR EXTERNAL FIXATION DEVICE

(75) Inventor: Michael Mullaney, Kinnelon, NJ (US)

(73) Assignee: Extraortho, Inc., Memphis, TN (US)

( * ) Notice: Subject to any disclaimer, the term of this patent is extended or adjusted under 35 U.S.C. 154(b) by 0 days.

(21) Appl. No.: 12/727,533

(22) Filed: Mar. 19, 2010

(65) Prior Publication Data

US 2010/0234845 A1    Sep. 16, 2010

Related U.S. Application Data

(63) Continuation of application No. 11/708,987, filed on Feb. 21, 2007, now Pat. No. 7,708,736.

(60) Provisional application No. 60/775,565, filed on Feb. 22, 2006.

(51) Int. Cl.
*A61F 5/04*    (2006.01)

(52) U.S. Cl. .......................... 606/59; 403/385

(58) Field of Classification Search .................. 24/485, 24/488–490, 499, 523, 524, 537, 538, 539, 24/563, 573.11, 574.1, 574.11, 580.11, 582.11, 24/582.12, 583.11, 587.1, 587.11, 589.1, 24/595.1, 598.1, 598.5, 599.3, 599.4, 599.6, 24/600.3, 600.7, 600.9, 602, 611, 629, 631; 248/124.2, 229.12, 27.3, 288.51, 292.14, 248/316.2, 316.3, 346.04, 74.2; 606/53–59; 403/385

See application file for complete search history.

(56) References Cited

U.S. PATENT DOCUMENTS

| | | | | |
|---|---|---|---|---|
| 1,706,215 | A * | 3/1929 | Davidson | 403/97 |
| 2,705,603 | A * | 4/1955 | Bitz et al. | 248/541 |
| 3,044,512 | A | 7/1962 | Jones | |
| 3,154,331 | A | 10/1964 | Engelhardt | |
| 3,373,465 | A * | 3/1968 | Johnson et al. | 24/490 |

(Continued)

FOREIGN PATENT DOCUMENTS

DE    2430234    1/1975

(Continued)

OTHER PUBLICATIONS

International Searching Authority/United States Patent Office, "Notification of Transmittal of the International Search Report and The Written Opinion of the International Searching Authority, or the Declaration," for PCT/US08/77800, mailed Dec. 2, 2008, 11 pages.

(Continued)

*Primary Examiner* — Eduardo C Robert
*Assistant Examiner* — Lynnsy Schneider
(74) *Attorney, Agent, or Firm* — Haynes and Boone LLP

(57) ABSTRACT

An articulation element consisting of a plurality of adjustable jaw pairs for the purposes of fixating the relative position of coupled bars and/or bone pins of an external bone fixator. Each of the adjustable jaws consists of a pair of hemispherical jaw elements contained within a spherical housing. A passage is eccentrically arranged through the jaw elements to accept the pin or bar. The jaw elements have interposed between them a spring element that serves to bias the jaw elements in the closed position. Pins serve to provisionally lock the jaw elements in the closed position. Spring loaded buttons act to release the pins thereby allowing the jaw elements to open accepting the pin or bar. The jaws are attached in a back to back fashion through the use of a threaded collar which acts as a turnbuckle pulling the jaws together when tightened.

48 Claims, 8 Drawing Sheets

U.S. PATENT DOCUMENTS

| | | | |
|---|---|---|---|
| 4,037,978 A * | 7/1977 | Connelly | 403/164 |
| 4,115,966 A * | 9/1978 | DeLee | 52/148 |
| 4,312,488 A * | 1/1982 | Pierron | 248/74.1 |
| 4,483,334 A | 11/1984 | Murray | |
| 4,620,533 A | 11/1986 | Mears | |
| 4,662,365 A | 5/1987 | Gotzen et al. | |
| 4,700,437 A * | 10/1987 | Hoshino | 24/456 |
| D295,725 S * | 5/1988 | Shioda | D8/396 |
| 4,817,897 A * | 4/1989 | Kreusel | 248/68.1 |
| 5,312,405 A * | 5/1994 | Korotko et al. | 606/278 |
| 5,427,465 A * | 6/1995 | Sato | 403/49 |
| 5,662,648 A | 9/1997 | Faccioli et al. | |
| 5,683,389 A | 11/1997 | Orsak | |
| 5,709,681 A | 1/1998 | Pennig | |
| 5,741,252 A | 4/1998 | Mazzio et al. | |
| 5,752,954 A | 5/1998 | Mata et al. | |
| 5,800,548 A * | 9/1998 | Martin et al. | 606/253 |
| 5,827,282 A | 10/1998 | Pennig | |
| 5,860,728 A | 1/1999 | Maglica | |
| 5,891,144 A | 4/1999 | Mata et al. | |
| 5,976,141 A | 11/1999 | Haag et al. | |
| 6,022,348 A | 2/2000 | Spitzer | |
| 6,080,153 A | 6/2000 | Mata et al. | |
| 6,102,911 A | 8/2000 | Faccioli et al. | |
| 6,217,577 B1 | 4/2001 | Hofmann | |
| 6,376,775 B1 * | 4/2002 | Leijon et al. | 174/128.1 |
| 6,386,786 B1 * | 5/2002 | Perlman et al. | 403/90 |
| 6,409,729 B1 | 6/2002 | Martinelli et al. | |
| 6,500,177 B1 | 12/2002 | Martinelli et al. | |
| 6,637,082 B1 * | 10/2003 | Chang | 24/523 |
| 6,652,523 B1 | 11/2003 | Evrard et al. | |
| 6,702,814 B2 | 3/2004 | Walulik et al. | |
| 6,716,212 B1 | 4/2004 | Pickens | |
| 7,004,943 B2 * | 2/2006 | Ferrante et al. | 606/59 |
| 7,048,735 B2 | 5/2006 | Ferrante et al. | |
| 7,241,071 B2 * | 7/2007 | Carraher et al. | 403/164 |
| 7,241,074 B2 | 7/2007 | Thomke et al. | |
| 7,261,713 B2 | 8/2007 | Langmaid et al. | |
| 7,314,331 B1 * | 1/2008 | Koros et al. | 403/396 |
| 7,320,556 B2 * | 1/2008 | Vagn-Erik | 403/385 |
| 7,708,736 B2 | 5/2010 | Mullaney | |
| 2002/0042613 A1 * | 4/2002 | Mata | 606/59 |
| 2002/0061225 A1 * | 5/2002 | Boucher et al. | 403/386 |
| 2002/0165543 A1 | 11/2002 | Winquist et al. | |
| 2004/0044344 A1 | 3/2004 | Winquist et al. | |
| 2005/0113831 A1 * | 5/2005 | Franck et al. | 606/61 |
| 2006/0229602 A1 | 10/2006 | Olsen | |
| 2006/0229603 A1 | 10/2006 | Olsen | |
| 2006/0287652 A1 | 12/2006 | Lessig et al. | |
| 2007/0038217 A1 * | 2/2007 | Brown et al. | 606/57 |
| 2007/0049932 A1 * | 3/2007 | Richelsoph et al. | 606/61 |

FOREIGN PATENT DOCUMENTS

| | | |
|---|---|---|
| WO | WO 90/11055 | 10/1990 |
| WO | WO-92/12683 | 8/1992 |
| WO | WO-98/51227 | 11/1998 |
| WO | WO-99/25264 | 5/1999 |

OTHER PUBLICATIONS

Swiss Patent Office, Application No. 03 891/90-6, titled "Fixateur externe," Applicant —Jaquet Orthopedie S.A., filed Dec. 16, 1991, 34 pages.

* cited by examiner

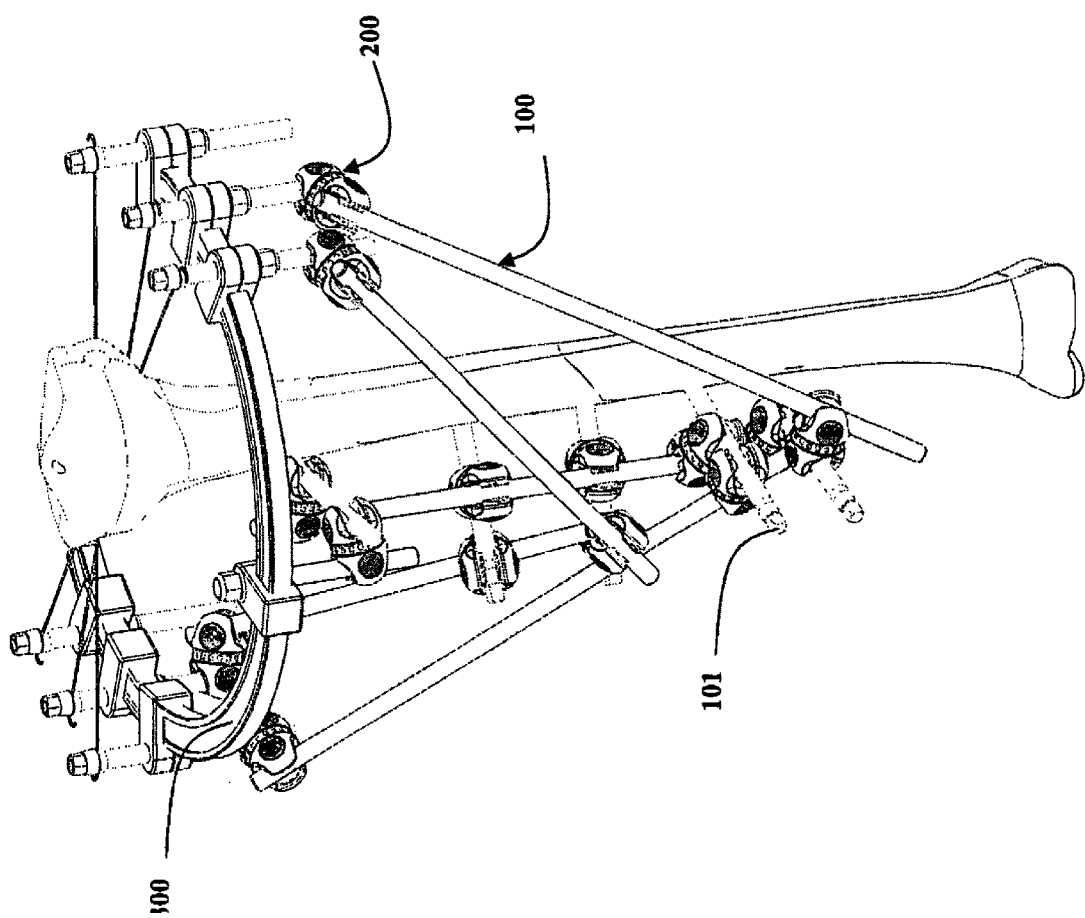

ARTICULATION APPARATUS FOR EXTERNAL FIXATION DEVICE

This application claims the benefit of U.S. Provisional Application No. 60/775,565 filed Feb. 22, 2006, and is a continuation of U.S. patent application Ser. No. 11/708,987, filed Feb. 21, 2007, U.S. Pat. No. 7,708,736, which are incorporated herein by reference in their entirety.

FIELD OF THE INVENTION

This innovation relates to an articulation element employed in the fixation of cylindrical components, namely bone pins and bar systems, utilized in the field of external fixation.

BACKGROUND OF THE INVENTION

External fixation devices typically include external frames which are used in conjunction with bone pins which are surgically placed into the bone fragments to be repaired or immobilized to promote healing. Such external fixation systems allow for particular placement of the bone pins that hold the bone fragment into which they are inserted, as there are often characteristics in the affected area that require delicate placement of pins such as proximity to nerves or arteries, or around joints.

The field of external fixation varies widely comprising many different types of apparatus. Typically bone pins are inserted through the soft tissue into the bone fragments; devices are then affixed to the pins and serve to connect the various fragments in such a way as to maintain correct anatomic position during the healing process. As is often the case, placement of the bone pins must be carefully selected to avoid damaging structures such as blood vessels, nerves, tendons, etc. Additionally consideration must be given to the structural integrity of the bone stock in combination with geometric stability considerations of the final construct.

Earlier fixation systems required prior assembly (complete or partial). One such know system uses a clamping type articulation element for the relative positioning of fixation bars and bone pins of an external fixation device. A drawback of such a device is that the articulation elements require being mounted on the fixation bars or the pins via their ends in advance of attachment. Until the clamping mechanism in such device is locked, the components are not held firmly and can move with respect to one another, making it difficult to hold all components in their proper relative orientation prior to or during final locking of the device.

Other known external fixation devices have been developed where the components of the external fixation devices are assembled after the pins have been inserted into the optimum position with respect to the bone fragment to be held and the tissue surrounding them. Typically the fixation bars making up the frame of the fixation device are then placed between the bone pins and articulation elements are used to connect the bars and the pins. It is often necessary that these articulation elements allow the bars or pins to be held at variable angles.

To address these concerns while providing maximum utility and ease of use; manufacturers have sought to develop fixation devices that allow for the placement of the bone pins to be independent of the external supporting structures that ultimately connect the pins together. In complex fractures there is often a need to place many pins, either because there are many fragments, or due to the poor quality of the bone and/or the nature of the fracture. Many pins, many of which will present themselves in different attitudes and inclinations, create a challenge when it comes time to connect them to the external structure. For this reason it is imperative to provide as many degrees of freedom when constructing an articulation element.

A simple analog to this condition is the case of the simply supported beam having more than 2 simple supports. This condition is characterized as being overly constrained. Unless the beam or the foundation is of sufficient flexibility it is impossible to share the load evenly across all of the multiple supports. To provide a flexible beam would defeat to goal of external fixation; we therefore need to provide a support system in the way of articulation elements that have the placement flexibility to evenly support the external structure.

One known prior art system describes an articulation component having two cylindrical joints with a revolute joint interposed between them. The characteristic mobility of this construct is two translations and three rotations for a total of five degrees of freedom. A known such system describes a similar device with the exception that the interposed revolute joint is replaced with a spherical joint. The characteristic mobility of this construct is two translations and five rotations for a total of 7 degrees of freedom. One could argue that more than 6 degrees of freedom is redundant and to some extent that is true but these extra degrees of freedom, redundant or not, make the placement of the device more flexible. This added spherical joint does however come at some expense, namely the pin to bar centerline distance must be increased, which makes for a bulkier construct while at the same time increasing the moment loading on the joints themselves.

The foregoing is believed to describe prior art systems as set forth, for example, in U.S. Pat. Nos. 6,080,153 and 7,048,735 (so called Jet-X Unilateral Fixation System), and EP 0321472.

SUMMARY OF THE INVENTION

The present invention provides advancements in the state of the relevant art by, inter alia, providing a an articulation element employed in the fixation of cylindrical components, namely bone pins and bar systems, utilized in the field of external fixation.

In accordance with one aspect of the present invention, the present invention aims to provide greater placement flexibility in a more compact construct than is presently available. It comprises the placement of fixation elements on either side of a fracture. These fixation elements are commonly referred to as pins, whereby one or more pins are screwed into a bone. One or more pins are located on either side of a fracture and connected to a bar via a clamp and/or a clamping system. The present invention relates to connecting pins with one or more bars in order to fixate a fracture. Such bars may also be connected to other bars or structures, if needed. In connecting pins to rods, it is advantageous to have mobility in a clamping system to allow for ease of placement and/or post placement manipulation.

One illustrative embodiment of the present invention comprises two (2) independent but connected clamp jaws, each clamp jaw being set in a clamp housing. Each clamp jaw comprises two (2) clamp jaw halves. The clamp jaw halves are shaped such that a clamp jaw is able to open and close around a bar or pin. In this embodiment of the present invention, the clamp jaw is able to clamp around a bar, while simultaneously, a connected corresponding clamp jaw is able to pivot about an axis normal to the axis of a pin or bar that is being clamped. Clamp jaw halves may be circular in shape to surround a pin or bar with a circular cross section. The clamp jaw halves may also be shaped to correspond to the cross section of the shape of the pin or bar being clamped. In another embodiment of the present invention, the clamp jaws may also be connected such that the clamp jaws also allows a bar or pin to rotate and approximately and/or equal to 20 degrees while clamped to allow for greater range and ease of positioning.

In alternative embodiments of the present invention, a spring is used to bias each clamp jaw half into the closed and/or clamped position. Each clamp jaw half is held in place by a jaw pin which engages a corresponding hole. In one embodiment of the present invention, the corresponding hole may comprise a specially milled shape and/or form. The jaw pins serve to limit the amount of travel of the clamp jaw halves and to lock the clamp jaw halves into the closed and/or clamped position. The jaw pins are preloaded into a locked position whereby the jaw pins are engaged with the hole in the jaw halves with a disc spring. The disc spring acts like a pressure plate spring and is made up of a series of radial levers connected around a periphery. Spring levers hold each jaw pin in place and allow each jaw pin to come into contact with a release button. The release button is concentric with the jaw pin and the disc spring. Application of an axial force on the release buttons causes retraction of the jaw pins in the opposite direction. When pressure is applied to the release buttons, such pressure causes the jaw pins to disengage from the clamp jaw halves, allowing the clamp jaw halves to open around the bar or pin. Removal of pressure will cause the jaw pins to re-insert into the holes in the clamp housing and a bar or pin may be placed in the clamp jaws and locked into place. A bar in a clamp jaw is able to rotate and slide about an axis orthogonal to the corresponding pin axis and pivot about the pin axis.

In the illustrative embodiment of the present invention, two (2) clamp housings are connected to each other by a collar. The collar has an interior diameter which comprises both a right hand female thread and left hand female thread. Each clamp housing also comprises a corresponding right male thread and a left male thread which attach the clamp housings to the collar. The clamp housings may be keyed to each other such that the clamp housings are limited in rotation to 180 degrees relative to each other. This prevents the clamp housings from having an unequal thread engagement in the collar and limits unnecessary range of motion.

In another embodiment of the present invention, each clamp housing with corresponding clamp jaw, also comprises two corresponding clutch plates which slide along an axis concentric with a collar. The clutch plates are keyed to the clamp housing in which they slide and bear against the clamp jaw halves and corresponding clutch plate. When the collar is tightened, the collar forces the clutch plates against each other and forces the clamp jaw halves into a respective clamp housing. The action locks the clamp jaw halves to the bar or pin and the clamp housings to each other fixating the clamping system. In other embodiments of the present invention, the clutch plates may be smooth and/or may be serrated.

In embodiments of the present invention for applications with low load and/or for accommodating less weight, the clutch plates could be smooth. This may be useful for fractures of the upper extremities. In such embodiment of the present invention directed at low load applications, the clamp jaw halves could comprise a smooth outer spherical surface. In yet another embodiment of the present invention for applications with higher load and/or accommodating more weight, the clutch plates could be serrated and/or comprise clamp jaw halves that may comprise a fish scale and/or textured outer surface. In another embodiment of the present invention, a collar and clamp housings may comprise a tapered form and/or threaded diameters, for example, pipe thread, whereby in addition to bringing the two clamp housings together axially, the threaded diameters would squeeze the clamp bodies radially further tightening and clamping the clamp jaw halves.

Advantages of the present invention comprise the following: the present invention allows for one-handed application; includes one lock per joint; allows for greater degrees of freedom in mounting; allows for gross manipulation; accommodates multiple indications; comprises few components; and requires minimal training.

It will be appreciated by those skilled in the art that the foregoing brief description and the following detailed description are exemplary and explanatory of this invention, and are not intended to be restrictive thereof or limiting of the advantages which can be achieved by this invention. Thus, the accompanying drawings, referred to herein and constituting a part hereof, illustrate preferred embodiments of this invention, and, together with the detailed description, serve to explain the principles of this invention.

BRIEF DESCRIPTION OF THE DRAWINGS

Additional aspects, features, and advantages of the invention, both as to its structure and operation, will be understood and will become more readily apparent when the invention is considered in the light of the following description of illustrative embodiments made in conjunction with the accompanying drawings, wherein:

FIG. 8 is a perspective view of an illustrative external fixation system using the articulation element of the present invention for use on a long bone application.

DETAILED DESCRIPTION OF THE PREFERRED EMBODIMENT

The external fixation system of the present invention includes an articulation element employed in the fixation of cylindrical components, namely bone pins and bar systems. Its structure and functional details will be discussed in detail below in the context of an illustrative embodiment and with reference to the figures provided.

Figure 1:
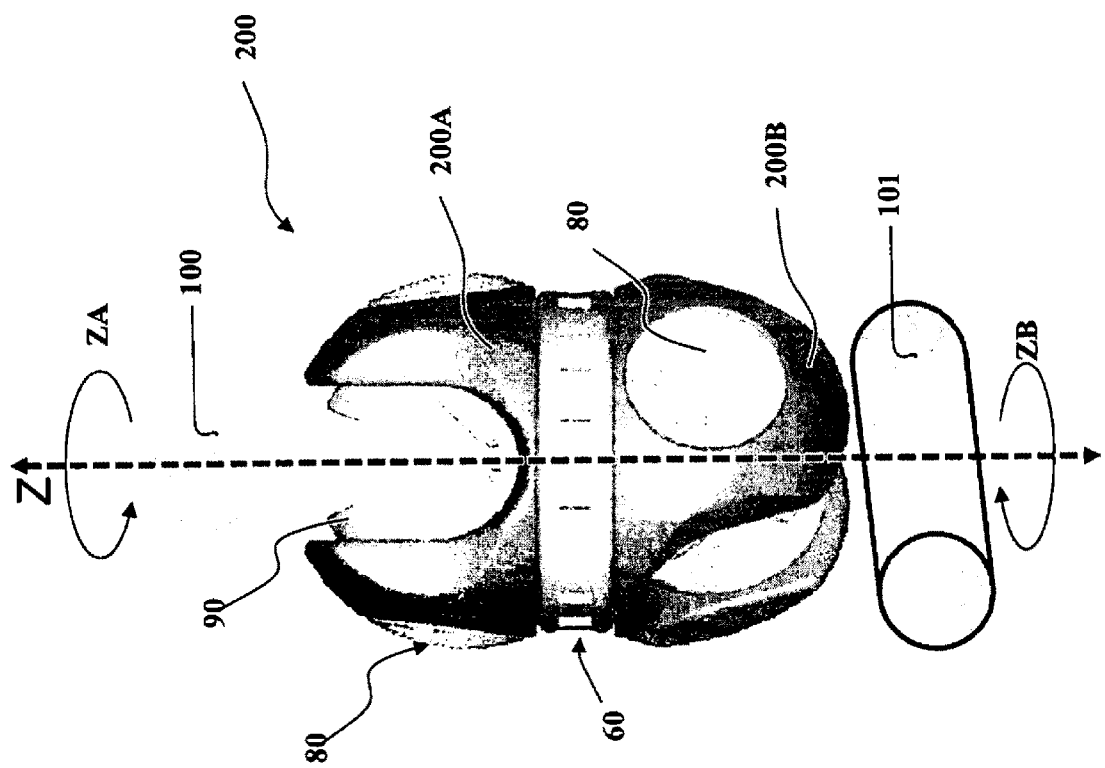
FIG. 1 is an isometric view of an articulation element according to an illustrative embodiment of the present invention.
Figure 2:
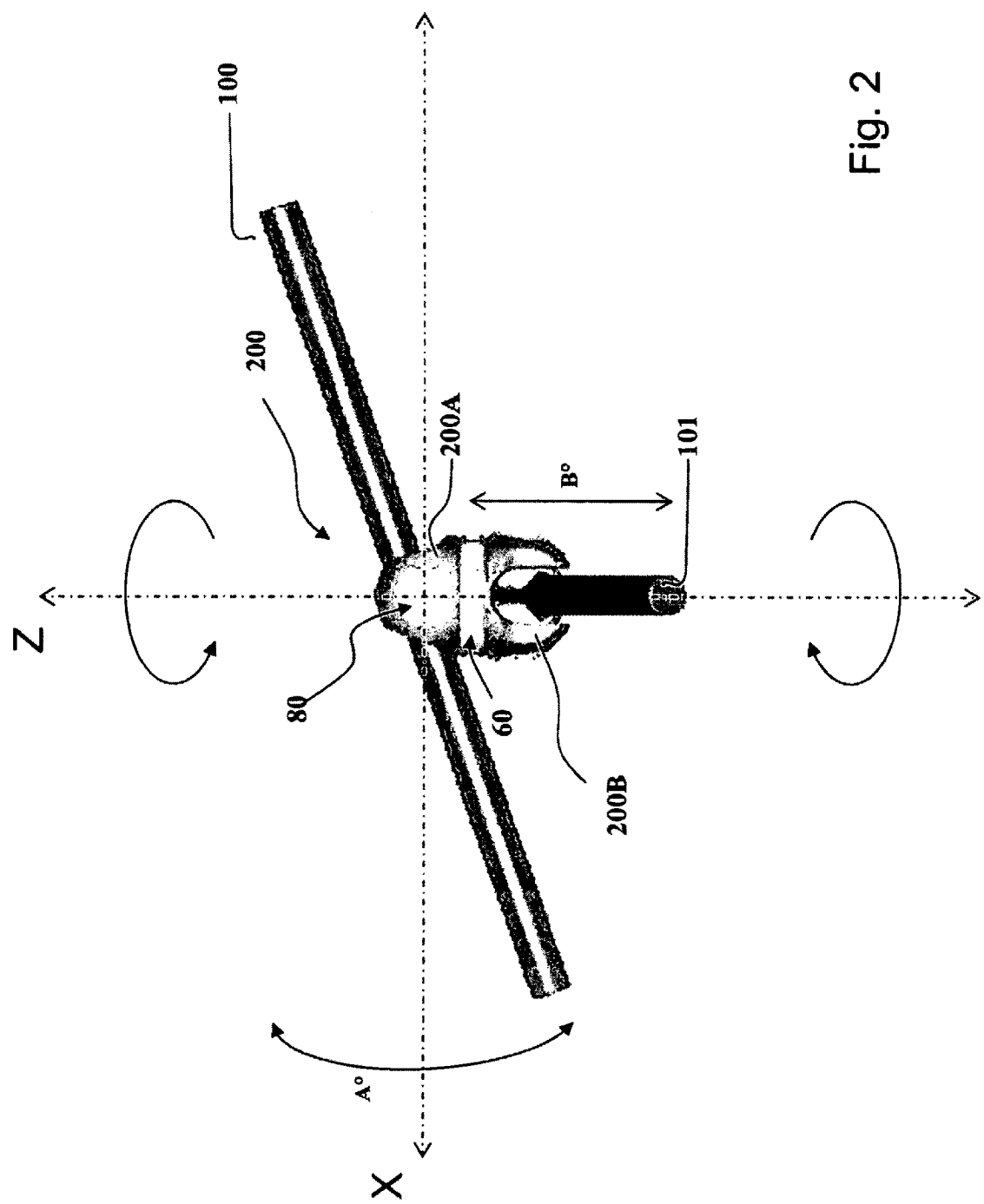
FIG. 2 is a second isometric view of the articulation element of FIG. 1.

FIGS. 1 and 2 show isometric views of an articulation element 200 according to an illustrative embodiment of the present invention.

The articulation element 200 consists of a pair of back-to-back spherical clamping mechanisms 200A and 200B that act to apply clamping pressure to cylindrical bars and/or pins shown conceptually as 100 and 101. The clamping mechanisms themselves consist of a pair of spherical jaw elements 90 within each of the spherical clamping mechanisms. Release buttons 80 allow the preloaded jaw elements 90 to relax to receive or release a rod or pin 100. Each mechanism 200A and 200B freely rotates about axis Z (i.e., in either rotational direction about the Z axis) as shown by arrows ZA and ZB. Lock ring 60 is used to lock the relative positions of 200A and 200B as will be described in detail below.

As shown in FIG. 2, bars 100 and 101 are shown in place in the clamping mechanisms 200A and 200B. Spherical jaw elements 90 (together forming an adjustable jaw pair) are disposed within the clamping mechanisms 200A and 200B such that they allow elevation of the respective bars mounted therein. Bar 100, shown mounted within mechanism 200A, can elevate through an angle A° about the X axis as shown in FIG. 2. (While elevation only about the X axis of bar 100 in mechanism 200A is shown, similar elevation of bar 101 in mechanism 200B through an angle B° about a Y axis (not shown) will be understood. The Y axis is not necessarily in any predetermined relation to the X axis, for example perpendicular to X.).

Figure 3:
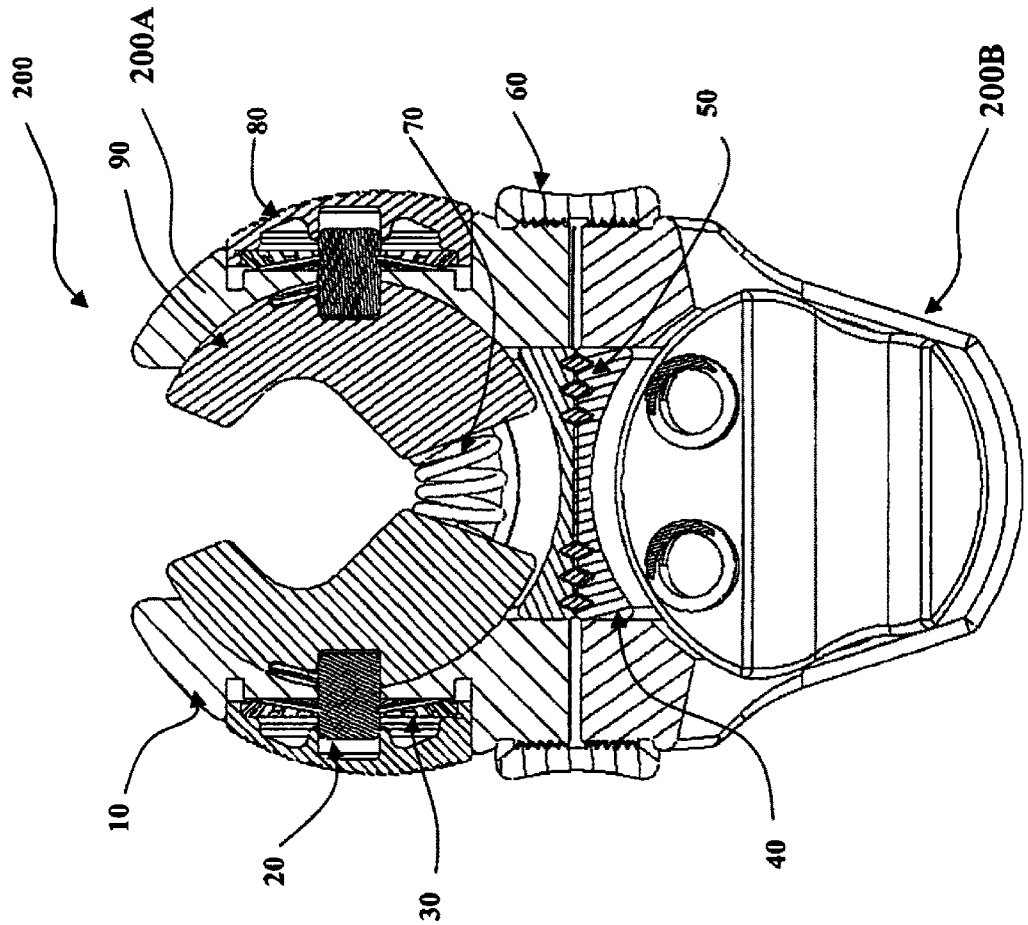
FIG. 3 is a representation of the articulation element of FIGS. 1 and 2 shown in schematic cross section.
Figure 4:
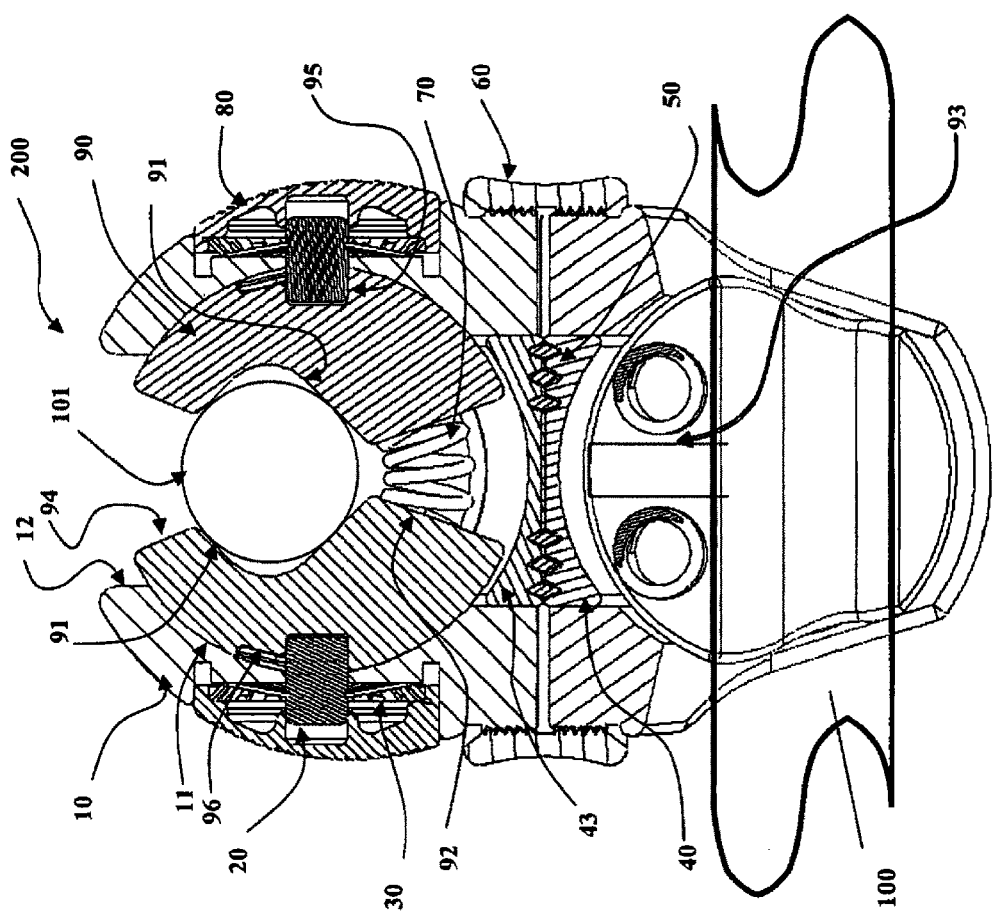
FIG. 4 is a close up representation of the articulation element of FIGS. 3.

In further detail and with reference to FIGS. 3-7, the articulation element 200 consists of a pair of back-to-back spherical clamping mechanisms or members that act to apply clamping pressure to cylindrical bars and/or pins shown conceptually as 100 and 101 (FIG. 4). The clamping mechanisms themselves consist of a pair of spherical jaw elements 90 that are held with in a spherical socket 11 (FIG. 4) within the clamp housing 10. Located eccentrically from the spherical jaw, an angular or Gothic arch type passage is machined to form the clamping or friction surfaces 91 (FIG. 4). Teeth, not shown, could if desired also be used on these surfaces 91 to provide a better gripping action.

Spherical jaw elements 90 are preloaded in a clamped or closed position by interposition of an elastic element 70 between the jaw elements 90, shown here as a coil spring 70. The coil spring 70 is seated within a cylindrical pocket 92 in each of the jaw elements 90. The elastic element 70 serves to bias the jaw elements 90 into the closed or clamped position around bar element 101. A tang and clevis arrangement between the two jaw elements, shown as a groove 93 (FIG. 4) constrains the jaw elements to rotate open and closed in a plane such that the pin and/or bar, 100, 101 can be accepted once pressure is applied to face 94 of each jaw element 90 (FIG. 4). Pressure on face 94 acts to open the jaw elements 90. Once the pin and/or bar 100, 101 is seated the elastic element 70 forces the jaw elements 90 to rotate closed.

Figure 6:
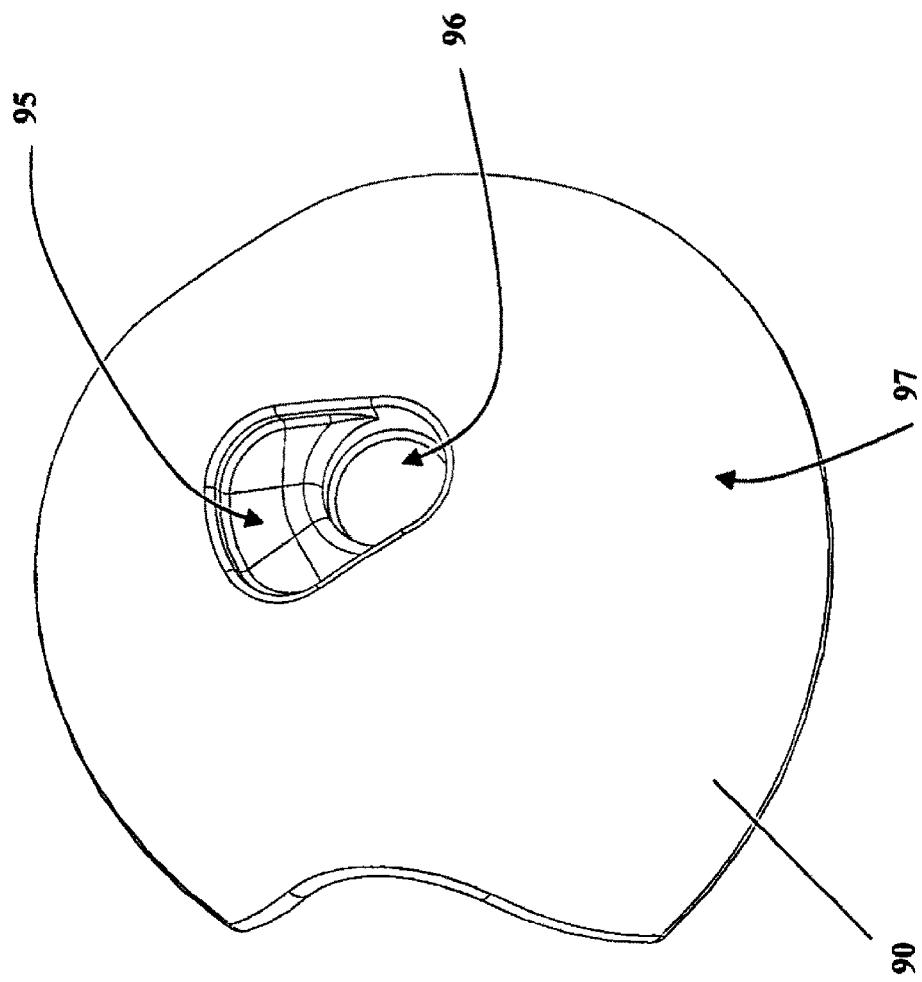
FIG. 6 is a view of the pin slot in one of the jaw elements of the articulation element of FIG. 3.
Figure 7A:
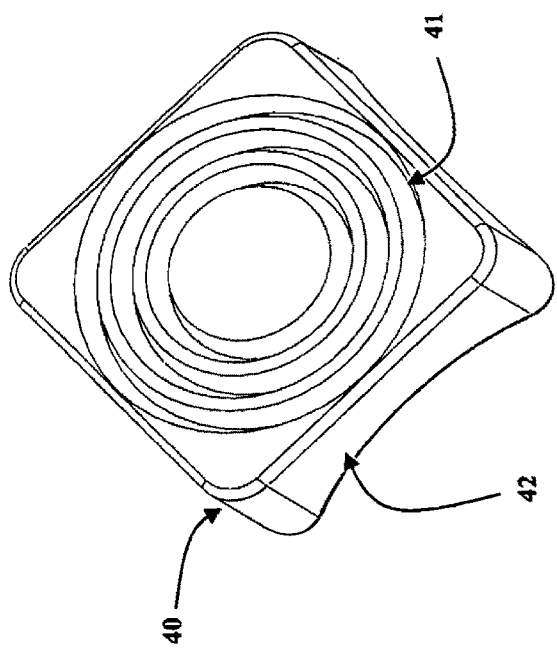
FIGS. 7A AND 7B are views of the clutch plate of the articulation element of FIG. 3.
Figure 7B:
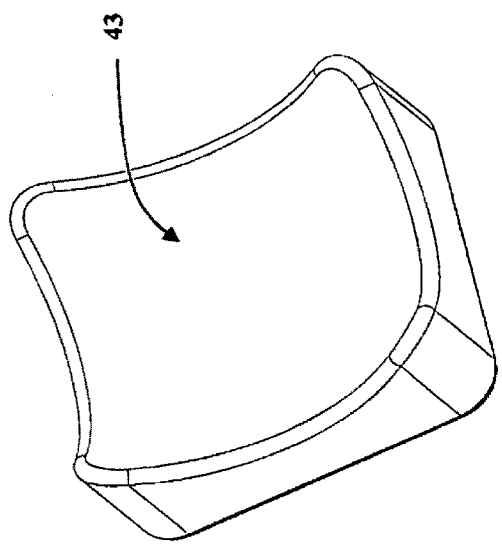

Pins 20 engage both the clamp housing 10 and the jaw elements 90 and serve to limit the range of mobility of the jaw elements 90 such that the mouth of the jaw elements 90 (formed between faces 94 of jaw elements 90) does not rotate out of the opening 12 (FIG. 4) of the clamp housing 10 by fitting into the milled recess 95 (FIGS. 4 and 7). Fully engaged, these pins 20 keep the jaw elements 90 in the closed position while still allowing for the rotation of the jaw elements 90 about the axis of the pins 20 by fitting into the cylindrical recess 96 (FIGS. 4 and 6).

Figure 5:
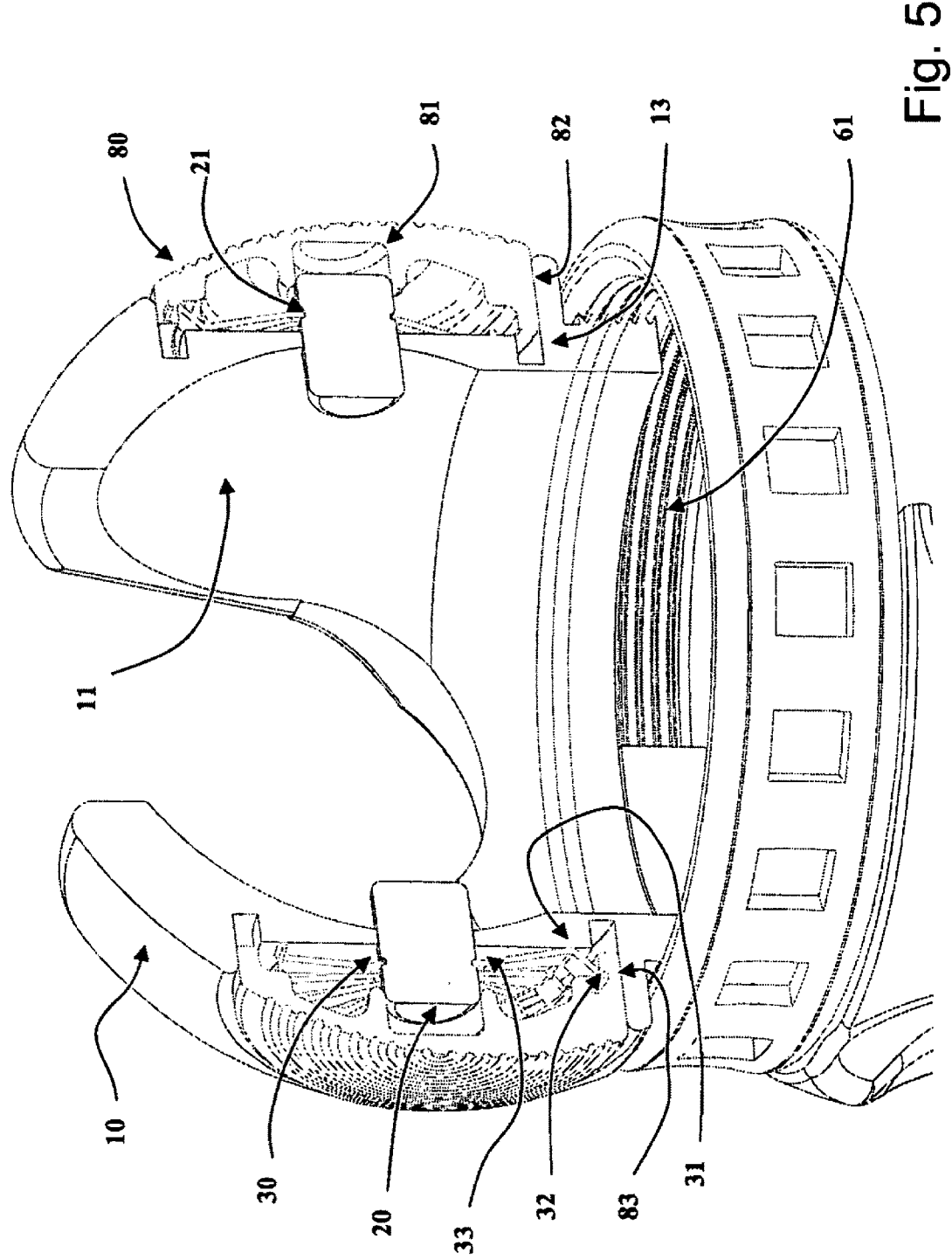
FIG. 5 is a cut away view of the release mechanism of the articulation element of FIGS. 1 and 2.

With reference to FIGS. 3, 4 and 5, a single point parallel release mechanism allows pins 20 to be retracted and engaged by means of a button 80 and disk spring mechanism 30. The button 80 is guided within cylindrical bore 13 in the clamp housing 10. A cylindrical bore 81 within the button 80 accepts and guides the pin 20. A disk spring 30 fashioned in such a way as to have a radial array of levers the outer diameter 32 of which is fitted within a circumferential groove 83 within the button 80. The inner diameter 33 of the disk spring 30 engages the pin 20 in circumferential grove 21. Application of force to the button 80 acts on the outer diameter 32 of the disk spring 30 which acts as a lever pivoting about fulcrum 31 which bears on the clamp housing. This action applies a force opposite in direction to that which was applied to the button to circumferential grove 21 of the pin 20 causing the pin 20 to retract allowing the jaw elements 90 to open in order to accept the pin and/or bar 100, 101. Releasing the force on the buttons 80 allows the pins to re-engage the cylindrical bore 96 of the jaw elements 90 keeping them in the closed position.

Once a pin and/or bar 100, 101 is engaged with both sets of jaw elements 90 the pins and/or bars 100, 101 are still free to slide and rotate relative to the jaw passage 91 while the jaw/pin/bar 90, 100, 101 assemblage is allowed to pivot about the pin 20 axis. Additionally either half of the articulation element 200 is allowed to rotate up to 180 degrees about the axis of lock ring 60.

To fixate the articulation element 200 lock ring 60 is tightened; having both a left hand and right hand female thread 61 on the ID it engages the corresponding threads on the clamp housing 10 drawing the two halves of the articulation assembly 200 together. As the two halves come together pressure is applied to the clutch plates 40 which bind clutch rings 50 into the corresponding clutch plate 40 on the other side. (See also FIGS. 6A and 6B) The pressure effectively keeps one clutch plate 40 from rotating relative to the other and the flat sides 42 key into the clamp housing 10. The spherical side 43 of 40 also applies pressure to the spherical surface of the jaw elements 97 (FIG. 7) wedging the jaw elements 90 in the clamp housing 10 which applies clamping pressure to the pins and/or bars 100, 101.

FIG. 8 shows an illustrative embodiment of the present invention where the articulation elements described herein are used in an external fixation system for a long bone application. Several rods 100 and pins 101 are shown being connected via articulation elements 200 of the present invention and fixation ring 300. Any number of pins or rods in combination with articulation elements 200 and ring 300 may be used as will be understood by one skilled in the art.

The present invention has been illustrated and described with respect to specific embodiments thereof, which embodiments are merely illustrative of the principles of the invention and are not intended to be exclusive or otherwise limiting embodiments. For instance, although the description provided hereinabove along with the accompanying drawings illustrate particular embodiments incorporating one or a few features of the present invention, those skilled in the art will understand in view of the hereinabove disclosure that alternative configurations can be devised and implemented, as well as other designs capable of achieving the purpose and benefits of the discussed aspects of the invention.

Accordingly, although the above description of illustrative embodiments of the present invention, as well as various illustrative modifications and features thereof, provides many specificities, these enabling details should not be construed as limiting the scope of the invention, and it will be readily understood by those persons skilled in the art that the present invention is susceptible to many modifications, adaptations, variations, omissions, additions, and equivalent implementations without departing from this scope and without diminishing its attendant advantages. It is further noted that the terms and expressions have been used as terms of description and not terms of limitation. There is no intention to use the terms or expressions to exclude any equivalents of features shown and described or portions thereof. It is therefore intended that the present invention is not limited to the disclosed embodiments but should be defined in accordance with the claims that follow.

What is claimed is:

1. An articulation element for an external fixation apparatus for treating a patient, the element having a longitudinal axis, said element comprising:
a first adjustable jaw pair configured to apply clamping pressure to capture
a first rigid element of the external fixation apparatus;
a second adjustable jaw pair configured to apply clamping pressure to capture a second rigid element of the external fixation apparatus; and
a coupling mechanism disposed between the first and second jaw pairs so as to allow the first jaw pair to rotate relative to the second jaw pair about the longitudinal axis, the coupling mechanism being disposed at a first location on the longitudinal axis and comprising a first component having a first flat surface and a first substantially curved concave surface and a second component having a second flat surface and a second substantially curved concave surface, the first flat surface being engageable with the second flat surface,
wherein the first and second components are independent of and disposed between the first and second adjustable jaw pairs and are pivotable relative to each other about the longitudinal axis, and wherein the first and second adjustable jaw pairs are pivotable relative to the respective first and second components,
the first adjustable jaw pair disposed so as to pivot about a first transverse pivot axis, the first transverse pivot axis being displaced from the first location in a first direction along the longitudinal axis,
the second adjustable jaw pair disposed so as to pivot about a second transverse pivot axis, the second transverse pivot axis being displaced from the first location in a second direction different than the first direction,
wherein the substantially curved concave surfaces are each configured to engage against a respective one of the first and second adjustable jaw pairs and selectively limit movement of the first adjustable jaw pair and the second adjustable jaw pair about the respective first and second transverse pivot axes.

2. The articulation element of claim 1, comprising a locking mechanism structurally configured to lock the relative orientation of said first adjustable jaw pair to said second adjustable jaw pair.

3. The articulation element of claim 1, wherein the first transverse pivot axis intersects the longitudinal axis.

4. The articulation element of claim 3, wherein the second transverse pivot axis intersects the longitudinal axis.

5. The articulation element of claim 1, wherein the first component comprises a first substantially flat surface facing the second component.

6. The articulation element of claim 5, wherein the first substantially flat surface comprises impressions configured to aid in preventing relative movement of the first component and the second component.

7. The articulation element of claim 1, wherein the first substantially curved concave surface is a spherical surface.

8. The articulation element of claim 1, wherein the first substantially curved concave surface receives at least a part of the first adjustable jaw pair.

9. The articulation element of claim 1, wherein the first substantially curved concave surface is shaped to match at least a part of the first adjustable jaw pair.

10. The articulation element of claim 1, further comprising a first biasing member disposed to apply a biasing force that acts on the first adjustable jaw pair to bias jaws of the first adjustable jaw pair to a closed position.

11. The articulation element of claim 1, wherein the first rigid element of the external fixation apparatus is one of an external fixation bar having a convex surface and a bone pin having a convex surface, the first rigid element being sized for grasping between concave surfaces on jaws of the first adjustable jaw pair.

12. The articulation element of claim 1, comprising a locking mechanism structurally configured to lock the relative orientation of said first adjustable jaw pair to said second adjustable jaw pair, the locking mechanism being configured to simultaneously restrict rotational motion about the longitudinal axis and restrict pivot motion of the first adjustable jaw pair about the first transverse pivot axis.

13. The articulation element of claim 12, wherein the locking mechanism is structurally configured to further restrict pivot motion of the second adjustable jaw pair about the second transverse pivot axis.

14. The articulation element of claim 1, wherein each jaw of each adjustable jaw pair includes a concave surface forming an inner surface of the adjustable jaw pair, the concave surface comprising a tooth grip surface.

15. The articulation element of claim 1, wherein the coupling mechanism is disposed between and at substantially equal distances from the first and second adjustable jaw pairs.

16. An external fixation system comprising:
the articulation element of claim 1;
a bone pin as the first rigid element of the external fixation apparatus; and
a rigid rod as the second rigid element of the external fixation apparatus.

17. An articulation element for an external fixation apparatus for treating a patient, the element having a longitudinal axis, said element comprising:
a first articulation component comprising
a first adjustable jaw pair configured to apply clamping pressure to capture a first rigid element of the external fixation apparatus, and
a first rotational component adjacent the first adjustable jaw pair having a substantially flat surface and a substantially curved concave surface, the substantially curved concave surface facing the first adjustable jaw pair; and
a second articulation component comprising
a second adjustable jaw pair configured to apply clamping pressure to capture a second rigid element of the external fixation apparatus, and
a second rotational component adjacent the second adjustable jaw pair having a substantially flat surface and a substantially curved concave surface, the substantially curved concave surface facing the second adjustable jaw pair,
wherein the substantially flat surface of the first rotational component is engageable with the substantially flat surface of the second rotational component,
the second articulation component being rotatable about the longitudinal axis relative to the first articulation component,
the first adjustable jaw pair being pivotable relative to the first rotational component about a first transverse pivot axis,
the second adjustable jaw pair being pivotable relative to the second rotational component about a second transverse pivot axis,
wherein the substantially curved concave surface of the first rotational component is structurally configured to engage against a curved surface of the first adjustable jaw pair to selectively limit movement of the first adjustable jaw pair about the first transverse axis.

18. The articulation element of claim 17, comprising a locking mechanism structurally configured to lock the relative orientation of said first adjustable jaw pair to said second adjustable jaw pair.

19. The articulation element of claim 17, wherein the first transverse pivot axis intersects the longitudinal axis.

20. The articulation element of claim 19, wherein the second transverse pivot axis intersects the longitudinal axis.

21. The articulation element of claim 17, wherein the first substantially flat surface comprises impressions configured to aid in preventing relative movement of the first rotational component and the second rotational component.

22. The articulation element of claim 17, wherein the first substantially curved concave surface is a spherical surface.

23. The articulation element of claim 17, wherein the first substantially curved concave surface receives at least a part of the first adjustable jaw pair.

24. The articulation element of claim 17, wherein the first substantially curved concave surface is shaped to match at least a part of the first adjustable jaw pair.

25. The articulation element of claim 17, further comprising a first biasing member disposed to apply a biasing force that acts on the first adjustable jaw pair to bias jaws of the first adjustable jaw pair to a closed position.

26. The articulation element of claim 17, wherein the first rigid element of the external fixation apparatus is one of an external fixation bar and a bone pin.

27. The articulation element of claim 17, comprising a locking mechanism structurally configured to lock the relative orientation of said first artculation component to said second artculation component, the locking mechanism being configured to simultaneously restrict rotational motion about the longitudinal axis and restrict pivot motion of the first adjustable jaw pair about the first transverse pivot axis.

28. The articulation element of claim 27, wherein the locking mechanism is structurally configured to further restrict pivot motion of the second adjustable jaw pair about the second transverse pivot axis.

29. The articulation element of claim 17, wherein each adjustable jaw pair includes a curvate surface forming an inner surface of the adjustable jaw pair, the curvate surface comprising a tooth grip surface.

30. The articulation element of claim 17, wherein the first and second rotational components are disposed between and at substantially equal distances from the first and second adjustable jaw pairs.

31. An external fixation system comprising:
the articulation element of claim 17;
a bone pin as the first rigid element of the external fixation apparatus; and
a rigid rod as the second rigid element of the external fixation apparatus.

32. An articulation element for an external fixation apparatus for treating a patient, the element having a longitudinal axis, said element comprising:
a first articulation component comprising
a first adjustable jaw pair configured to apply clamping pressure to capture a first rigid element of the external fixation apparatus, and
a first rotational component adjacent the first adjustable jaw pair, the first rotational component having a first flat surface and a first substantially curved concave surface, the first adjustable jaw pair being pivotable about a first transverse axis so as to pivot relative to the first rotational component; and
a second articulation component comprising
a second adjustable jaw pair configured to apply clamping pressure to capture a second rigid element of the external fixation apparatus, and
a second rotational component adjacent the second adjustable jaw pair, the second rotational component having a first flat surface and being shaped to interface with at least one jaw of the second adjustable jaw pair, the second adjustable jaw pair being pivotable about a second transverse axis so as to pivot relative to the second rotational component;
wherein the first articulation component is rotatable relative to the second articulation component about the longitudinal axis, the relative rotation occurring at a rotational location on the longitudinal axis, and
wherein the first articulation component is structurally arranged such that the first transverse axis is spaced from the rotational location in a first direction along the longitudinal axis,
and wherein the second articulation component is structurally arranged such that the second transverse axis is spaced from the rotational location in a second direction different than the first direction,
wherein the first flat surface is engageable with the second flat surface, and the substantially curved concave surface of the first rotational component is structurally configured to engage against a curved surface of the first adjustable jaw pair to selectively limit movement of the first adjustable jaw pair about the first transverse axis.

33. The articulation element of claim 32, comprising a locking mechanism structurally configured to lock the relative orientation of said first adjustable jaw pair to said second adjustable jaw pair.

34. The articulation element of claim 32, wherein the first transverse pivot axis intersects the longitudinal axis.

35. The articulation element of claim 34, wherein the second transverse pivot axis intersects the longitudinal axis.

36. The articulation element of claim 32, wherein the first rotational component and the second rotational component are independent of and disposed between the first and second adjustable jaw pairs.

37. The articulation element of claim 32, wherein the first rotational component comprises a first substantially flat surface facing the second rotational component.

38. The articulation element of claim 37, wherein the first substantially flat surface comprises impressions configured to aid in preventing relative movement of the first rotational component and the second rotational component.

39. The articulation element of claim 32, wherein the first substantially curved concave surface is a spherical surface.

40. The articulation element of claim 32, wherein the first substantially curved concave surface receives at least a part of the first adjustable jaw pair.

41. The articulation element of claim 32, wherein the first substantially curved concave surface is shaped to match at least a part of the first adjustable jaw pair.

42. The articulation element of claim 32, further comprising a first biasing member disposed to apply a biasing force that acts on the first adjustable jaw pair to bias jaws of the first adjustable jaw pair to a closed position.

43. The articulation element of claim 32, wherein the first rigid element of the external fixation apparatus is one of an external fixation bar and a bone pin.

44. The articulation element of claim 32, comprising a locking mechanism structurally configured to lock the relative orientation of said first rotational component to said second rotational component, the locking mechanism being configured to simultaneously restrict rotational motion about the longitudinal axis and restrict pivot motion of the first adjustable jaw pair about the first transverse pivot axis.

45. The articulation element of claim 44, wherein the locking mechanism is structurally configured to further restrict pivot motion of the second adjustable jaw pair about the second transverse pivot axis.

46. The articulation element of claim 32, wherein each adjustable jaw pair includes a curvate surface forming an inner surface of the adjustable jaw pair, the curvate surface comprising a tooth grip surface.

47. The articulation element of claim 32, wherein the rotational location on the longitudinal axis is disposed between and at substantially equal distances from the first and second adjustable jaw pairs.

48. An external fixation system comprising:
the articulation element of claim 32;
a bone pin as the first rigid element of the external fixation apparatus; and
a rigid rod as the second rigid element of the external fixation apparatus.

* * * * *